United States Patent
Franck et al.

(10) Patent No.: US 10,598,582 B2
(45) Date of Patent: Mar. 24, 2020

(54) ORTHOGONAL SUPERPOSITION RHEOMETER

(71) Applicant: WATERS TECHNOLOGIES CORPORATION, Milford, MA (US)

(72) Inventors: Aloyse J. P. Franck, Milford, MA (US); John P. Berting, Milford, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 0 days.

(21) Appl. No.: 14/778,888

(22) PCT Filed: May 22, 2014

(86) PCT No.: PCT/US2014/039079
§ 371 (c)(1),
(2) Date: Sep. 21, 2015

(87) PCT Pub. No.: WO2014/190120
PCT Pub. Date: Nov. 27, 2014

(65) Prior Publication Data
US 2016/0047727 A1    Feb. 18, 2016

Related U.S. Application Data (60) Provisional application No. 61/826,576, filed on May 23, 2013.

(51) Int. Cl.
*G01N 11/16* (2006.01)
*G01N 11/14* (2006.01)

(52) U.S. Cl.
CPC .......... *G01N 11/162* (2013.01); *G01N 11/14* (2013.01); *G01N 11/16* (2013.01)

(58) Field of Classification Search
CPC ....... G01N 11/162; G01N 11/14; G01N 11/16
USPC ...................................................... 73/54.28
See application file for complete search history.

(56) References Cited

U.S. PATENT DOCUMENTS

| 2,796,758 A | 6/1957 | Myers et al. |
|---|---|---|
| 4,214,475 A | 7/1980 | Carter et al. |
| 2009/0056423 A1 | 3/2009 | Franck et al. |

FOREIGN PATENT DOCUMENTS

| JP | 57166162 U | 10/1982 |
|---|---|---|
| JP | 09318520 A | 12/1997 |

OTHER PUBLICATIONS

Extended European Search Report dated Dec. 16, 2016 in European Patent Application No. 14801844.3.
(Continued)

*Primary Examiner* — Nimeshkumar D Patel
*Assistant Examiner* — Rodney T Frank
(74) *Attorney, Agent, or Firm* — Schmeiser, Olsen & Watts LLP (57) ABSTRACT

An orthogonal superposition rotational rheometer that applies a rotational torque and an orthogonal axial oscillatory stress to a fluid. The rheometer uses a cylindrical bob in a double wall cup to apply shear rotational and axial forces to the fluid. Openings in the top section of the cylindrical bob reduce surface tension effects on the force measurement. Fluid pumping effects at the bottom of the rheometer's double wall cup are minimized by openings in the inner wall of the double wall cup that allow fluid to be displaced when the bob moves downwards.

26 Claims, 10 Drawing Sheets

(56) References Cited

OTHER PUBLICATIONS

J. Zeegers et al., "A sensitive dynamic viscometer for measuring the complex shear modulus in a steady shear flow using the method of orthogonal superposition" Rheol Acta 34:606-621 (1995) Copyright—Steinkopff Verlag 1995.

J. Vermant et al., "Orthogonal superposition measurements using a rheometer equipped with a force rebalanced transducer," Rev. Sci. Instrum. 68 (11), 4090-4096 (1997) Copyright—1997 American Institute of Physics.

J.M. Simmons, "A servo-controlled rheometer for measurement of the dynamic modulus of viscoelastic liquids," J.Sci. Instrum., 1996, vol. 43, pp. 887-892.

International Preliminary Report on Patentability dated Sep. 30, 2014 in International Application No. PCT/US2014/039079.

Office Action dated Oct. 18, 2016 in Japanese Patent Application No. 2016-514167, and translation thereof.

ORTHOGONAL SUPERPOSITION RHEOMETER

BACKGROUND

This application is the U.S. National Stage of International Application No. PCT/US2014/039079, filed May 22, 2014, entitled "Orthogonal Superposition Rheometer," which claims priority to U.S. Provisional Application No. 61/826,576, filed May 23, 2013, both of which are incorporated by reference herein in their entireties.

The present embodiments relate to rotational rheometers that may be used to measure rheological properties of materials such as the viscosity or modulus of the materials.

Rheometers may be used to measure the properties of materials such as oils, dispersions, suspensions, emulsions, adhesives, biological fluids, polymers, gels, pastes, slurries, melts, resins, powders or mixtures of the foregoing. Specific examples of such materials include asphalt, chocolate, blood, drilling mud, lubricants, oils, greases, photoresists, liquid crystals, liquid cements, elastomers, thermoplastic polymers and coatings.

As used herein, the term "rheometer" shall include rheometers, viscometers, viscosimeters and any other instrument that may be used to measure the viscoelastic properties of fluids or powders. Also, as used herein, the term "fluid" shall include liquids, oils, dispersions, suspensions, emulsions, adhesives, biological fluids, polymers, gels, powders, pastes, slurries, melts, resins and mixtures of any of these materials, as well as any other materials that may be characterized according to their viscoelastic properties.

Rheological measurements in rotational rheometers are performed by applying a stress or deformation (rate) in a rotational direction. Rotational rheometers may apply a predetermined torque to a material in a rotational direction, and measure the resulting displacement of the material under test. Alternatively, they may measure the torque required to obtain a predetermined displacement.

In an orthogonal superposition rotational rheometer, an additional shear deformation (rate) or stress is applied in a second direction, normal to the rotational direction. This may be used, for example, to measure the effect of a strong shear flow on the rheological behavior of the material.

A test module for an orthogonal superposition rheometer may have a double wall cup retaining the test fluid and a cylindrical bob. The cylindrical bob is inserted between the inner and outer wall of the cup, providing the inner and outer circular shear surfaces for the fluid when either the cup or the cylindrical bob performs a rotational and/or an axial movement. In a typical test setup the cylindrical bob is attached to a torque/force transducer, but the bob could also be attached to a rotational/linear actuator.

SUMMARY

Embodiments of a double wall orthogonal superposition (OSP) rotational rheometer may apply rotational stress to the material under test, upon which is superimposed an orthogonal stress. This allows the application of a shear flow in the rotational direction and another shear flow simultaneously in the axial direction. Surface tension effects at the top of the rheometer's double wall cup are minimized by apertures in the top portion of the bob that reduce effects of the free liquid interface in the gap on the force measurement. Fluid pumping effects at the bottom of the rheometer's double wall cup are minimized by openings in the inner wall of the double wall cup that allow fluid to be displaced when the bob moves downwards.

Embodiments of the rotational rheometer have a double wall cup having an inner cylindrical wall and an outer cylindrical wall forming an annular chamber and a central cylindrical chamber; a cylindrical bob having a top disk portion, a hollow cylindrical portion and a shaft attached to the center of the top disk portion; a motor coupled to the double wall cup configured to rotate the double wall cup; and a transducer coupled to the cylindrical bob configured to impose axial oscillations on the cylindrical bob. The inner wall of the double wall cup comprises openings at its lower end that allow fluid communication from the annular chamber to the central cylindrical chamber. The cylindrical bob has apertures just below its top disk portion that circumscribe a substantial portion of the circumference of the top disk.

Embodiments of the rotational rheometer have a double wall cup with an inner cylindrical wall and an outer cylindrical wall forming an annular chamber and a central cylindrical chamber. They have a cylindrical bob which has a top disk portion, a hollow cylindrical portion, a shaft attached to the center of the top disk portion, and at least one leg at the top circumference of the hollow cylindrical portion attaching the hollow cylindrical portion to the top disk portion. These embodiments also have means for rotating the double wall cup and for imposing axial oscillations on the cylindrical bob. They also have means for measuring the torque required to rotate the double wall cup and means for measuring the normal force required to impose the axial displacement on the cylindrical bob. The cylindrical bob has apertures just below its top disk portion that circumscribe a substantial portion of the circumference of the top disk.

Embodiments of the test module for a rotational rheometer have a double wall cup with an inner cylindrical wall and an outer cylindrical wall forming an annular chamber and a central cylindrical chamber; and a cylindrical bob having a top disk portion, a hollow cylindrical portion and a shaft attached to the center of the top disk portion. The inner cylindrical wall of the double wall cup has openings at its lower end that allow fluid communication from the annular chamber to the central cylindrical chamber. The top disk portion of the cylindrical bob is connected to the hollow cylindrical portion of the cylindrical bob by two or more legs leaving apertures just below its top disk portion that circumscribe a substantial portion of the circumference of the hollow cylindrical portion.

Embodiments of the test module for a rotational rheometer have a double wall cup with an inner cylindrical wall, an outer cylindrical wall forming an annular chamber and a central cylindrical chamber, and a base. They have a cylindrical bob with a top disk portion, a hollow cylindrical portion and a shaft attached to the center of the top disk portion. The top disk portion of the cylindrical bob is connected to the hollow cylindrical portion of the cylindrical bob by at least two legs leaving apertures just below its top disk portion that circumscribe at least 80% of the circumference of the hollow cylindrical portion.

This summary is intended to provide an overview of the subject matter of the present invention, and is not intended to identify essential features or key elements of the subject matter, nor is it intended to be used to determine the scope of the claimed invention. The proper scope of the invention may be ascertained from the detailed description of the embodiments provided below, the figures referenced therein and the claims below.

Other structures, objects, features and advantages of embodiments of the present invention will be apparent to one of ordinary skill in the art upon examination and study of the following detailed description and the accompanying figures. It is intended that all such additional structures, features and advantages of the invention be included within this description and this summary, be within the scope of the embodiments and be protected by the claims set forth below.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS OF THE INVENTION

For clarity, the detailed descriptions herein describe certain exemplary embodiments, but the disclosure herein may be applied to any test module for a rheometer that comprises certain of the features described herein and recited in the claims. In particular, the following detailed description discusses exemplary embodiments of the orthogonal superposition rheometer.

Figure 1:
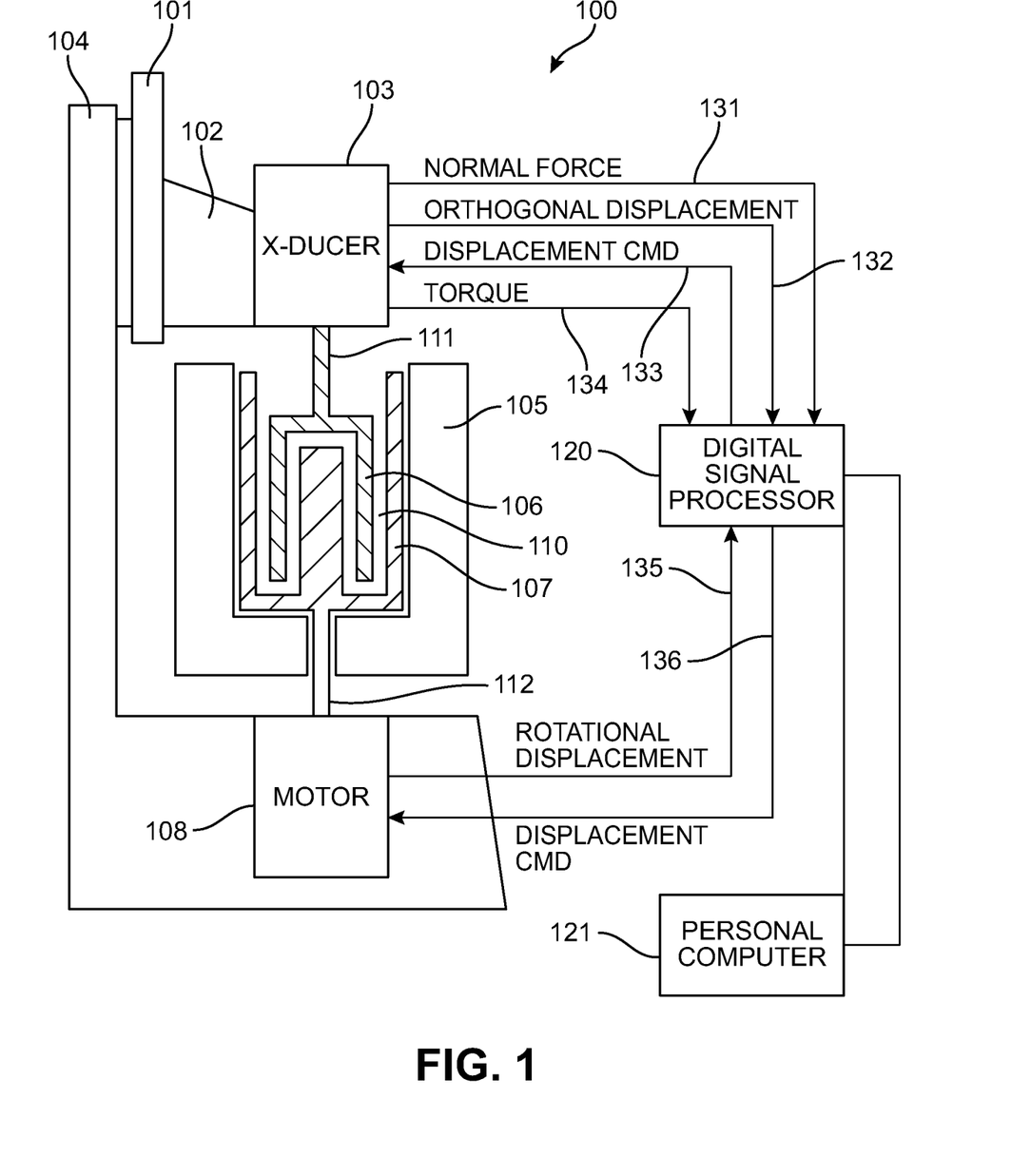
FIG. 1 is a schematic drawing of an OSP test module integrated into a typical rheometer.

FIG. 1 is a schematic diagram of an embodiment of an OSP test module integrated into a rotational rheometer. In the embodiment shown in FIG. 1, the rotational rheometer is a dual head rheometer with a force rebalance transducer. Other embodiments may use a single head rheometer with either an integrated active normal force actuator/transducer or a single head rheometer with integrated normal force actuator and a separate force sensor, as described below.

The basic operation of the example of an orthogonal superposition rheometer 100 shown in FIG. 1 is the simultaneous rotation of double wall cup 107 with the orthogonal oscillation of cylindrical bob 106. Cylindrical bob 106 fits within annular chamber 110 of double wall cup 107. Thus the material to be tested experiences rotational shear due to rotation of the double wall cup, and axial (i.e., vertical) shear due to the oscillation of cylindrical bob 106. The superposition of the rotational shear and the axial shear provides valuable information regarding the rheological properties of materials, such as their modulus and their viscosity.

FIG. 1 shows rheometer 100 with transducer 103, environmental control chamber 105, double wall cup 107, test chamber 110 and cylindrical bob 106 within enclosure 104. Bracket 102 supports transducer 103. Environmental control chamber 105 may be used to control the temperature of double wall cup 107 at temperatures that may range from, for example, −160° C. up to 600° C., using conventional heating and/or cooling devices. Motor 108 rotates double wall cup 107 via shaft 112. Transducer 103 applies an oscillatory vertical stress to the test material contained in double wall cup 107 via shaft 111 and cylindrical bob 106. In this embodiment, transducer 103 also measures the orthogonal axial force applied to the test sample, and measures the torque on cylindrical bob 106 due to the rotational motion of the material in double wall cup 107. Transducer 103 is mounted on slide 101, so that cylindrical bob 106 can be lifted to allow a material to be tested to be placed into test chamber 110. Transducer 103 applies an oscillatory vertical displacement to cylindrical bob 106 via shaft 111, and also measures the normal force required to effect that displacement.

The oscillatory motion applied by transducer 103 to shaft 111 may have a sinusoidal waveform, a triangular waveform, a sawtooth waveform, or a square waveform, or it may be any other periodic waveform. The ranges of amplitudes and frequencies that may be used are discussed below. The rotation of cup 107 may be continuous and unidirectional, or it may be oscillatory, as discussed below.

Digital signal processor 120 provides displacement commands 133 to transducer 103 and displacement commands 136 to motor 108. Digital signal processor 120 receives a signal 131 representative of the applied normal force, a signal 132 representative of the orthogonal displacement of shaft 111 and cylindrical bob 106, and a signal 134 from transducer 103 representative of the torque due to the rotation of cup 107. Digital signal processor 120 also receives a signal 135 representative of the rotational displacement applied to shaft 112 by motor 108. Digital signal processor 120 is under the control of personal computer 121, which includes a user interface through which an operator of rheometer 100 can enter parameters such as rotational velocity, rotational mode, applied normal force amplitude and frequency of the applied normal force.

The assembly of a double wall cup and a cylindrical bob, together with the necessary mechanical couplings and electrical connectors comprise an OSP test module. Such test modules may be used with rotational rheometers to measure certain rheological properties of materials such as the materials listed above.

Figure 2:
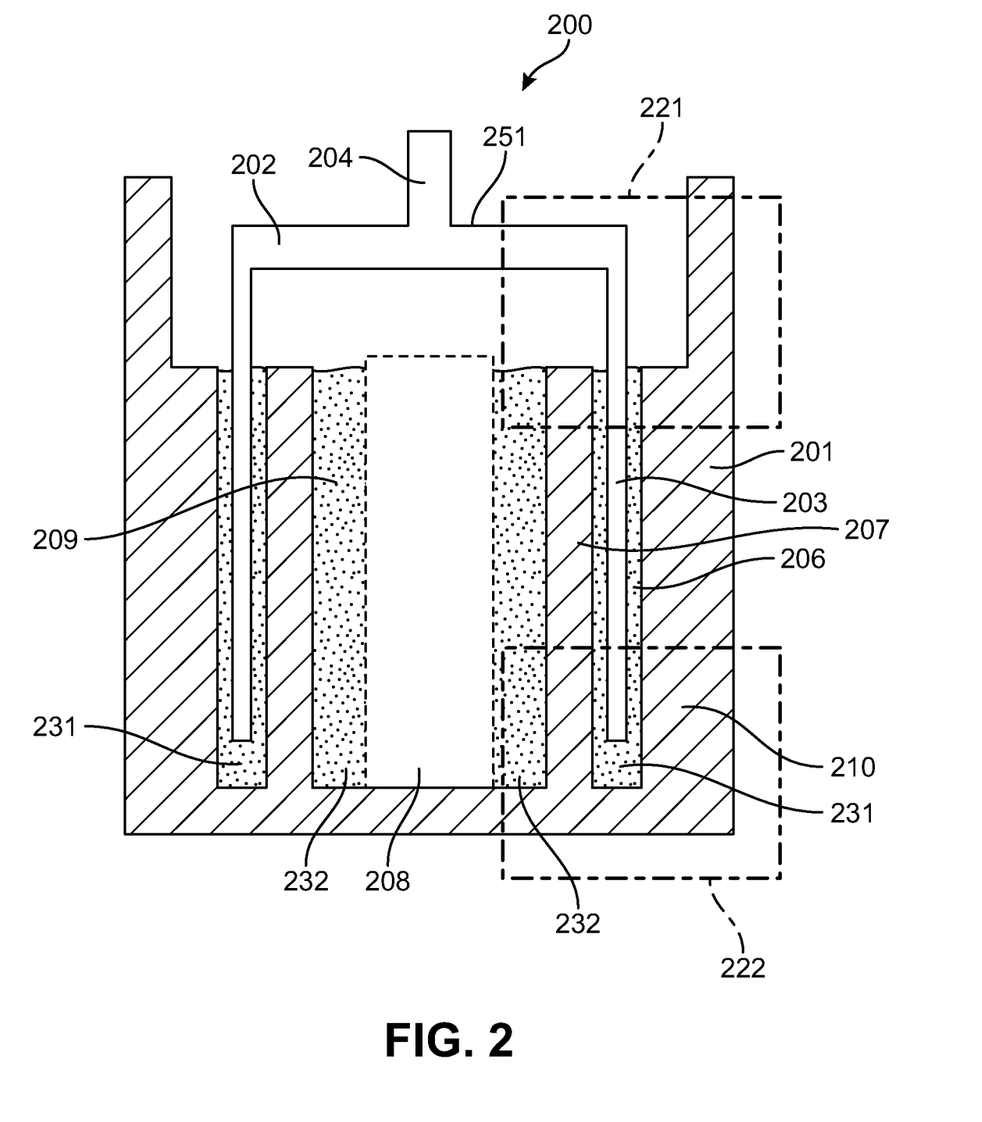
FIG. 2 is a schematic drawing of a double wall OSP test module.

FIG. 2 is a schematic drawing of a double wall OSP test module. Test module 200 has a double wall cup 201 with an outer wall 210 and an inner wall 207 forming an annular test chamber 206. It also has a cylindrical central chamber 209, which may optionally contain a cylindrical plug 208. Cylindrical bob 202 is inserted into annular chamber 206 of double wall cup 201, i.e., between the inner wall 207 and the outer wall 210 of double wall cup 201. The fluid to be tested is placed in annular test chamber 206.

Cylindrical bob 202 has a shaft 204, a top disk 251 and a hollow outer cylinder wall 203. Optionally, test module 200 may also have a plug 208 in cylindrical central chamber 209.

The primary function of plug 208 is simply to reduce the volume that may need to be filled up with fluids during measurements, as discussed below. However, it is not necessary, and is not generally recommended for most cases. Dashed lines 221 (at the upper part of test module 200) and 222 (at the lower part of test module 200) outline the portions of test module 200 that are discussed below. Annular chamber 206 is filled with the fluid sample 231 that is to be tested. Cylindrical central chamber 209 contains additional fluid 232, which may be the same fluid as the fluid sample to be tested 231, or may be a different fluid.

Figure 3:
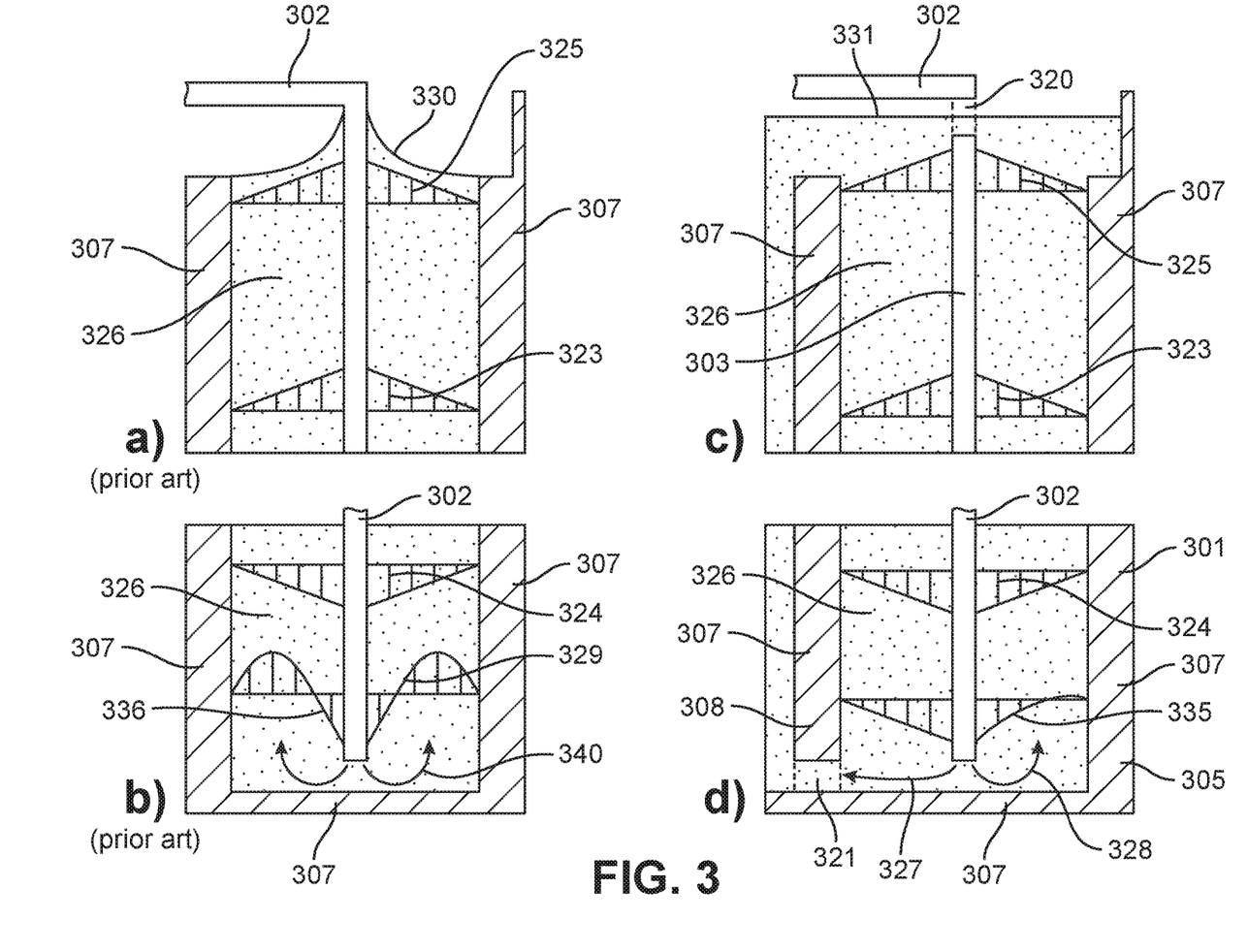
FIG. 3 is an expanded view of the sections of the OSP test module identified in FIG. 2.

FIG. 3 is a series of expanded views of the portion 221 and portion 222 outlined in FIG. 2 that compare an example of the present OSP test module to a prior art OSP test module. These views may be used to compare the fluid flows in a prior art test OSP module to the fluid flow in the present OSP test module. FIGS. 3(a) and 3(b) relate to the prior art OSP test module, while FIGS. 3(c) and 3(d) relate to embodiments of the present OSP test module. FIG. 3(a) illustrates fluid flow in the prior art OSP test module at the top portion 221 which is outlined in FIG. 2, in response to vertical movement of cylindrical bob 202. FIG. 3(b) illustrates fluid flow in the prior art OSP test module at the bottom portion 222 outlined in FIG. 2, in response to vertical movement of cylindrical bob 202.

As shown in FIG. 3(a), in the prior art test module, when cylindrical bob 302 moves upward, it induces upward fluid flows 323 and 325 in fluid 326. It also induces a meniscus 330 of the fluid against cylindrical bob 302. It has been discovered that surface tension effects of meniscus 330 contribute significantly and variably to the resistance to vertical oscillation of cylindrical bob 302. These surface tension effects are difficult to account for, and thus introduce errors into the measurement of the test fluid's resistance to vertical displacement as cylindrical bob 302 moves or oscillates within double wall cup 307.

As shown in FIG. 3(b), when cylindrical bob 302 moves downwards, it induces a complex fluid flow, in which the portions of the fluid 326 next to bob 302 flow downwards, but other portions further away from cylindrical bob 302 are forced upwards. The upward fluid flow occurs because the liquid displaced by the front of the moving bob is forced to flow back up in the axial (or vertical) direction in the gaps between the cylindrical bob 302 and the walls of double wall cup 307, disturbing the axial shear flow profile 324 imposed by the vertical axial motion of the bob 302.

Thus, as indicated by arrows in FIG. 3(b), the downward movement of bob 302 induces the fluid portion 324 (at the upper part of FIG. 3(b)) and the fluid portion 336 next to bob 302 (at the lower part of FIG. 3(b)) to flow downwards. However, fluid portions 329, which are further away from bob 302, are induced to flow upwards as illustrated by arrows 340. These complex fluid flows are difficult to account for, and therefore also introduce errors into the measurement of the test fluid's resistance to the vertical displacement of cylindrical bob 302 within double wall cup 307.

FIG. 3(c) illustrates fluid flow in an embodiment of the present test module at the top portion 221 which is outlined in FIG. 2, in response to vertical movement of cylindrical bob 302. FIG. 3(d) illustrates fluid flow in an embodiment of the present test module at the bottom portion 222 outlined in FIG. 2, in response to vertical movement of cylindrical bob 302. An example of cylindrical bob 302 in isolation is shown in perspective in FIG. 4.

Figure 4:
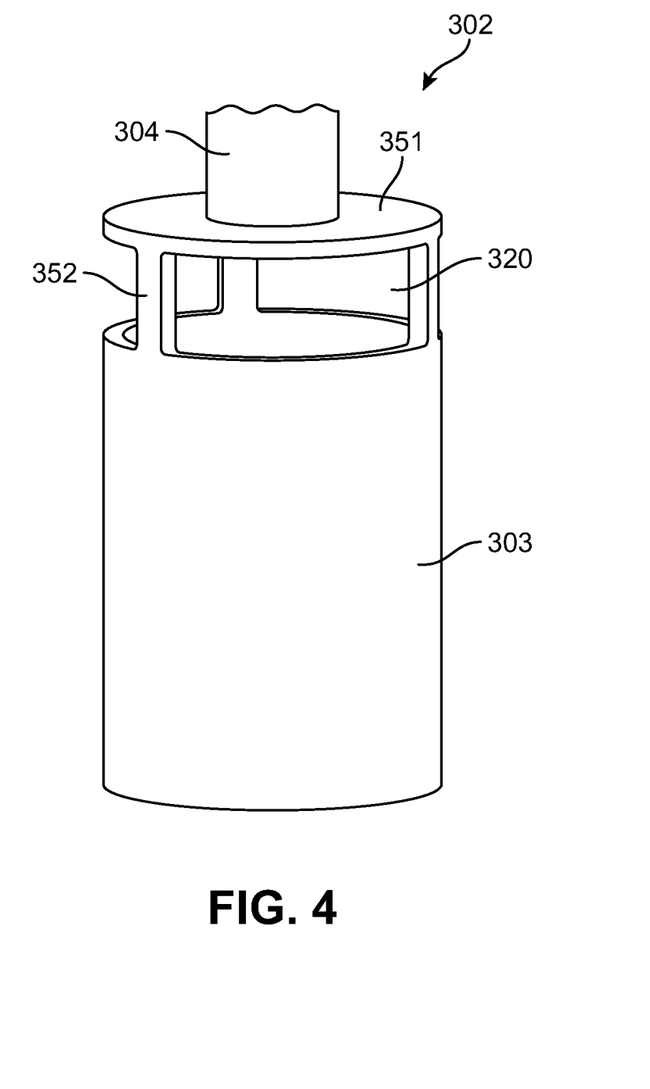
FIG. 4 is a perspective view of an embodiment of a cylindrical bob.

As shown in FIG. 4, cylindrical bob 302 has a shaft 304, a main hollow cylinder portion 303 and a top disk portion 351. Main cylinder portion 303 is connected to top disk portion 351 by legs 352. In the example shown in FIG. 4, top disk portion 351 is supported by three legs 352, but in other embodiments it could be supported by one, two, three, four or more legs. Between legs 352, cylindrical bob 302 has apertures 320. Legs 352 may be rectangular. Legs 352 may also be square, oval, trapezoidal or any other appropriate shape and thickness that can support hollow cylinder portion 303 as cylindrical bob 302 is displaced or oscillated axially and as double wall cup 307 rotates. In a typical example, legs 352 occupy less than 20% and preferably less than 10% of the circumference of cylindrical bob 302. In any event, apertures 320 circumscribe a substantial portion (more than 60%) of the circumference of the hollow cylinder.

Thus, as shown in FIG. 3(c), the top surface 331 of fluid 326 in double wall cup 307 is flat at the top across aperture 320, i.e., there is no meniscus formed at the apertures, as in the prior art OSP test module shown in FIG. 3(a). Although menisci are formed against legs 352 (shown in FIG. 4), the total surface area of the menisci is substantially reduced (in some embodiments by 60%, 80% or 90%) compared to the total surface area of the meniscus formed in the prior art OSP test module shown in FIG. 3(a). For that reason, surface tension effects due to menisci are greatly reduced compared to the surface tension effects due to the meniscus in the prior art OSP test module.

FIG. 3(d) shows an opening 321 in the inner wall 308 at the bottom of double wall cup 307. Rheometers with cups that have openings at the bottom are described in J. Vermant et al., "Orthogonal superposition measurements using a rheometer equipped with a force rebalanced transducer," Rev. Sci. Instrum. 68 (11), 4090 (1997). Opening 321 allows some of fluid 326 to flow into the center space of the double wall cup 307, as indicated by arrow 327, when cylindrical bob 302 is moved down. This reduces the pumping flow in the gap between the cylindrical bob 302 and the walls of double wall cup 307. Although there may be some upward flow as indicated by arrow 328 in the region between cylindrical bob 302 and outer wall 305 of double wall cup 307, that upward flow is limited, as shown by the downward flow in fluid portion 335.

Figure 5:
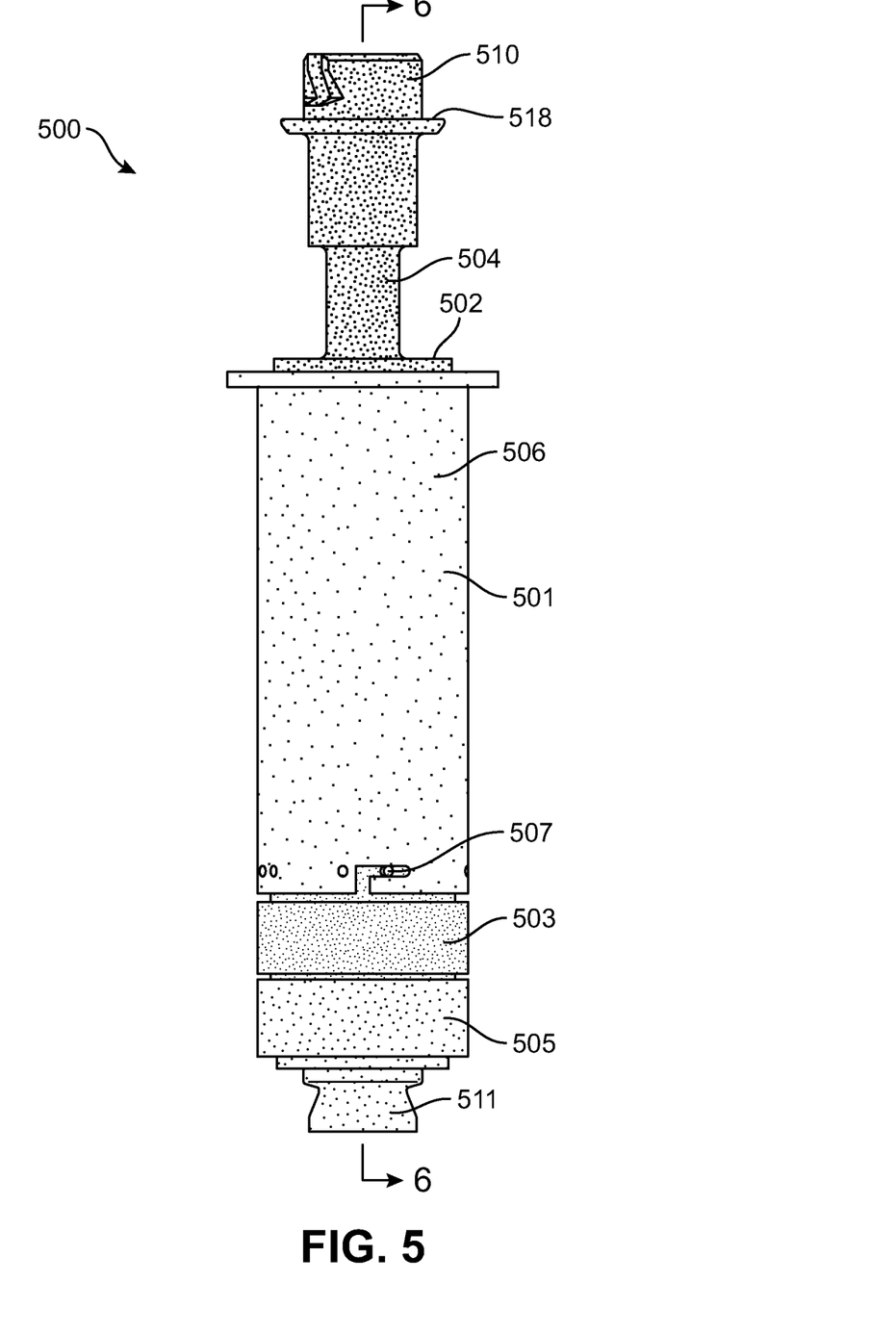
FIG. 5 is an assembly schematic drawing of the OSP test module.

FIG. 5 is a schematic assembly of an embodiment of the OSP test module 500. Cylindrical bob 502 fits inside double wall cup 501. Shaft 504 connects cylindrical bob 502 to coupling attachment 510. Flange 518 provides a surface for aligning the coupling of cylindrical bob 502 to a rheometer. Outer wall 506 of double wall cup 501 is removable to facilitate cleaning of the assembly. It is attached to the base 503 of the double wall cup 501 via a bayonet mount 507 so that it can be removed to clean the annular test chamber. Coupling attachment 511 connects double wall cup 501 to the rheometer. Base 505 of test module 500 supports the inner and outer walls of the double wall cup. As illustrated in FIG. 1, when test module 500 is mounted in a rheometer, at the top end cylindrical bob 502 is attached to a transducer, and at the bottom end, double wall cup 501 is attached to a motor.

Cylindrical bob 502 may be manufactured or assembled from, for example, titanium components. It may also be manufactured or assembled from stainless steel or other materials or from a combination of these or other materials. Double wall cup 501 is preferably manufactured or assembled from a material that has a high thermal conductivity (i.e., a material with a thermal conductivity greater than about 100 $W \cdot m^{-1} \cdot K^{-1}$) such as, for example, anodized aluminum, to help maintain a relatively uniform temperature distribution in the material under test. Base 505 of the test module may be manufactured from, for example, stainless steel.

Figure 6:
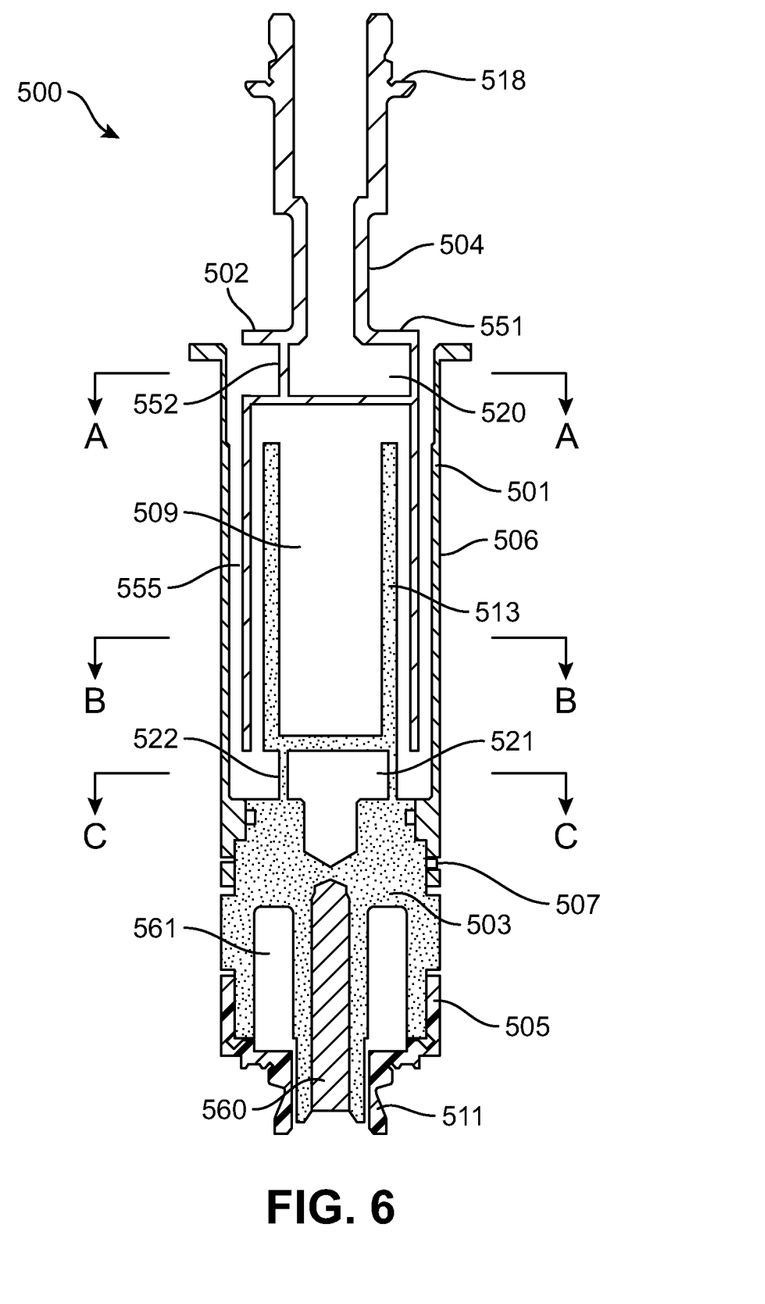
FIG. 6 is a vertical cross-section of the assembly module of FIG. 4, taken along the line identified by the arrows 6-6 identified in FIG. 5.

FIG. 6 is a vertical cross section of the assembly shown in FIG. 5, taken along the section indicated by the arrows in FIG. 5. FIG. 6 shows that cylindrical bob 502 has apertures 520 at its top end. Apertures 520 reduce the surface tension effects described above with reference to FIG. 3(a). Double wall cup 501 has openings 521 at its bottom end that allow some of the material being tested to flow into cylindrical central chamber 509, thus reducing the pumping effects described above with reference to FIG. 3(b). As in the example shown in FIG. 1, a motor (not shown in FIG. 6) coupled via coupling attachment 511 to double wall cup 501 applies rotational deformation to the material being tested, while a transducer (not shown in FIG. 6) applies an orthogonal oscillatory deformation in the axial (i.e., vertical) direction. Flange 518 facilitates the alignment of cylindrical bob 502 to the coupling attachment, as shown in FIG. 5.

The lower hollow cylindrical portion of cylindrical bob 502 fits between outer wall 506 and inner wall 513 of double-wall cup 501. Legs 552 attach the hollow cylinder portion of cylindrical bob 502 to top disk portion 551, which is attached to shaft 504. Outer wall 506 is removably attached to the base 503 of double wall cup 501 with bayonet mount 507. Base 505 of test module 500 is attached to base 503 and supports the inner and outer walls of the double wall cup 501.

Platinum resistance thermometer 560 is mounted in base 503 of test module 500 to measure the temperature of the fluid in the test module. The purpose of circumferential slit 561 in base 503 is to reduce the mass of the test module 500.

Figure 7:
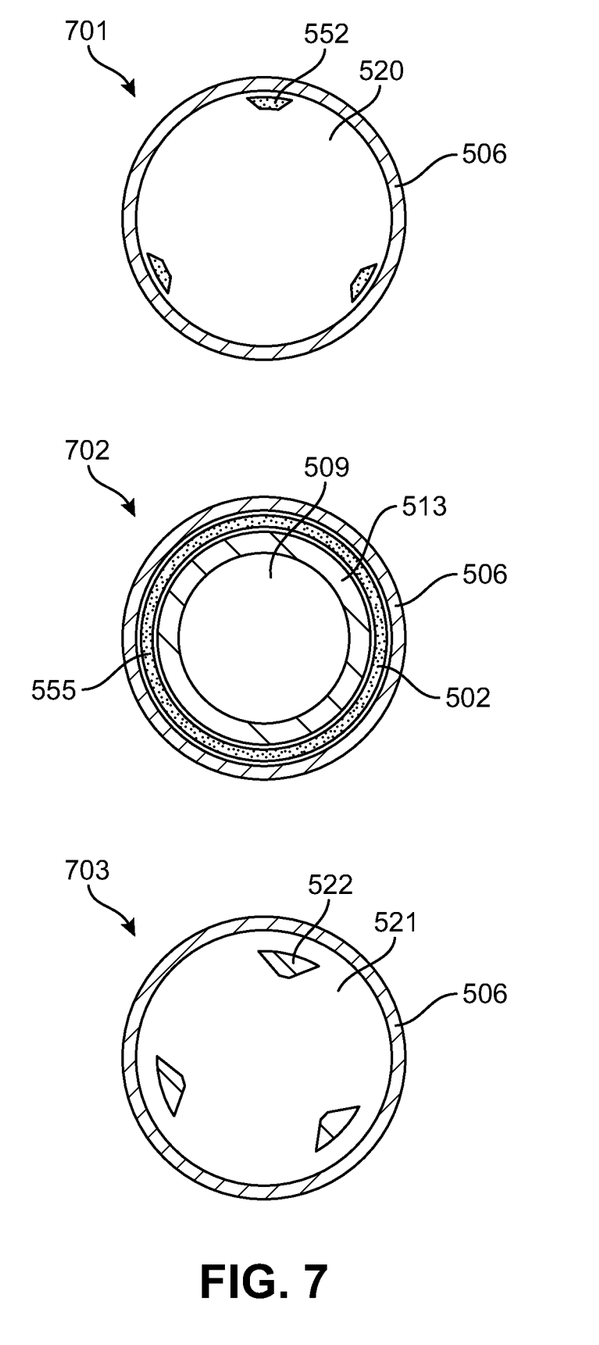
FIG. 7 shows three horizontal cross sections of the assembly module of FIG. 4, taken along the lines identified by the arrows A-A, B-B and C-C, respectively, of FIG. 6.

FIG. 7 shows three horizontal cross-sections of the assembly shown in FIG. 6, taken at the lines A-A, B-B and C-C, respectively, from top to bottom, as indicated in FIG. 6. The top A-A cross-section 701 shows outer wall 506 of the double wall cup and three legs 552 between apertures 520. As shown in this cross-section, in this embodiment the sides of legs 552 slant inwardly, thus facilitating the flow of fluid across legs 552. The middle B-B cross-section 702 shows cylindrical outer wall 506 and cylindrical inner wall 513 that form annular test chamber 555. This cross section also shows cylindrical central chamber 509 and cylindrical bob 502 in test chamber 555. The bottom C-C cross-section 703 shows cylindrical outer wall 506 and connecting portions 522 mechanically joining inner cylindrical wall 513 to the base of the double wall cup. Openings 521 between connecting portions 522 allow fluid flow of the material under test from annular test chamber 555 to cylindrical central chamber 509 when cylindrical bob 502 moves down.

In operation, a rheometer incorporating a test module as disclosed herein may be operated to impose an axial (i.e., vertical) oscillation on the cylindrical bob with an amplitude ranging from 0 µms to 500 µms at a frequency ranging from 0 Hz to 100 Hz (typically, 0.1-10 Hz). The cup rotation may be continuous, or the cup may be oscillated at a frequency ranging up to 100 Hz, with an amplitude ranging from 0.1 micro-radians up to a small fraction of a revolution, e.g. up to 10 milliradians.

Figure 8:
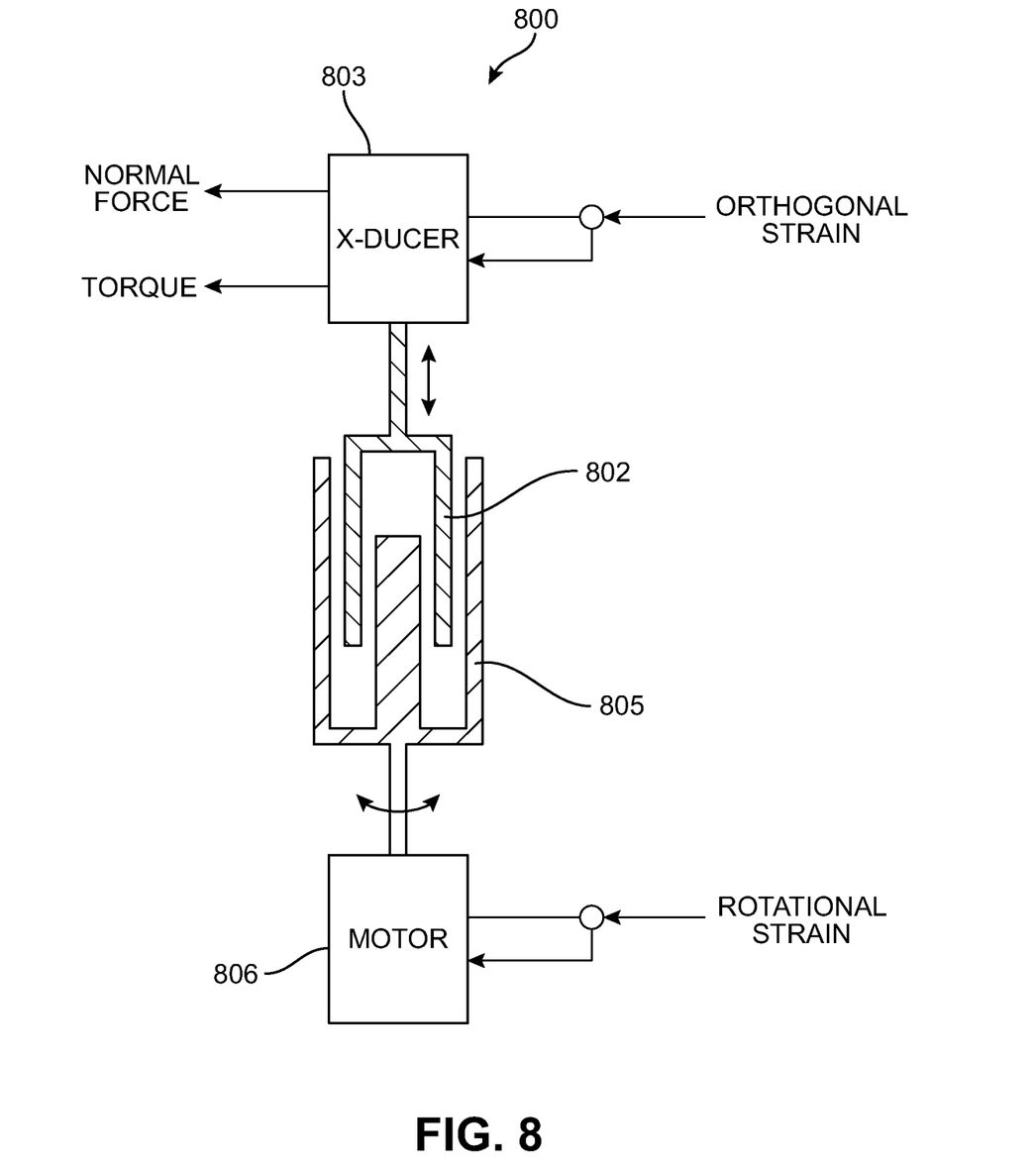
FIG. 8 is a schematic drawing of an OSP test module, mounted on a dual head rheometer with a force rebalance transducer.
Figure 9:
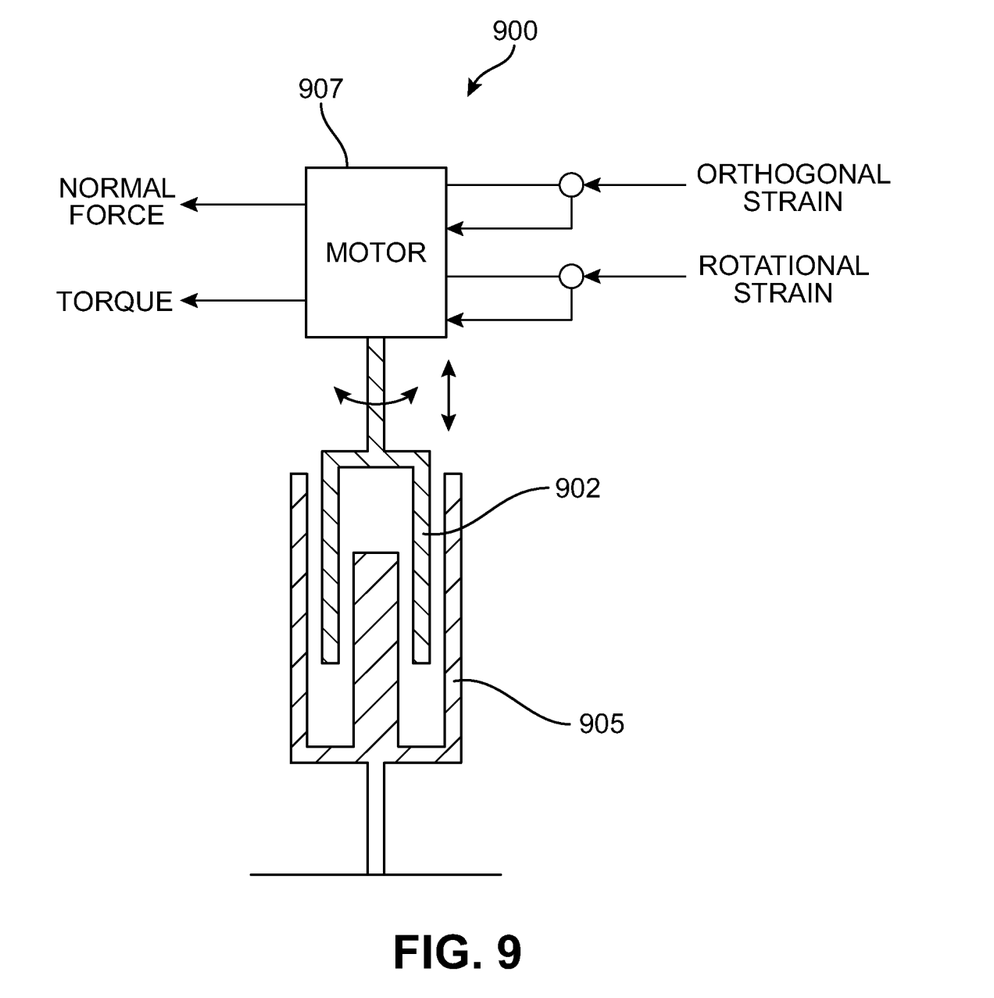
FIG. 9 is a schematic drawing of an OSP test module mounted on a single head rheometer with an active normal force transducer.
Figure 10:
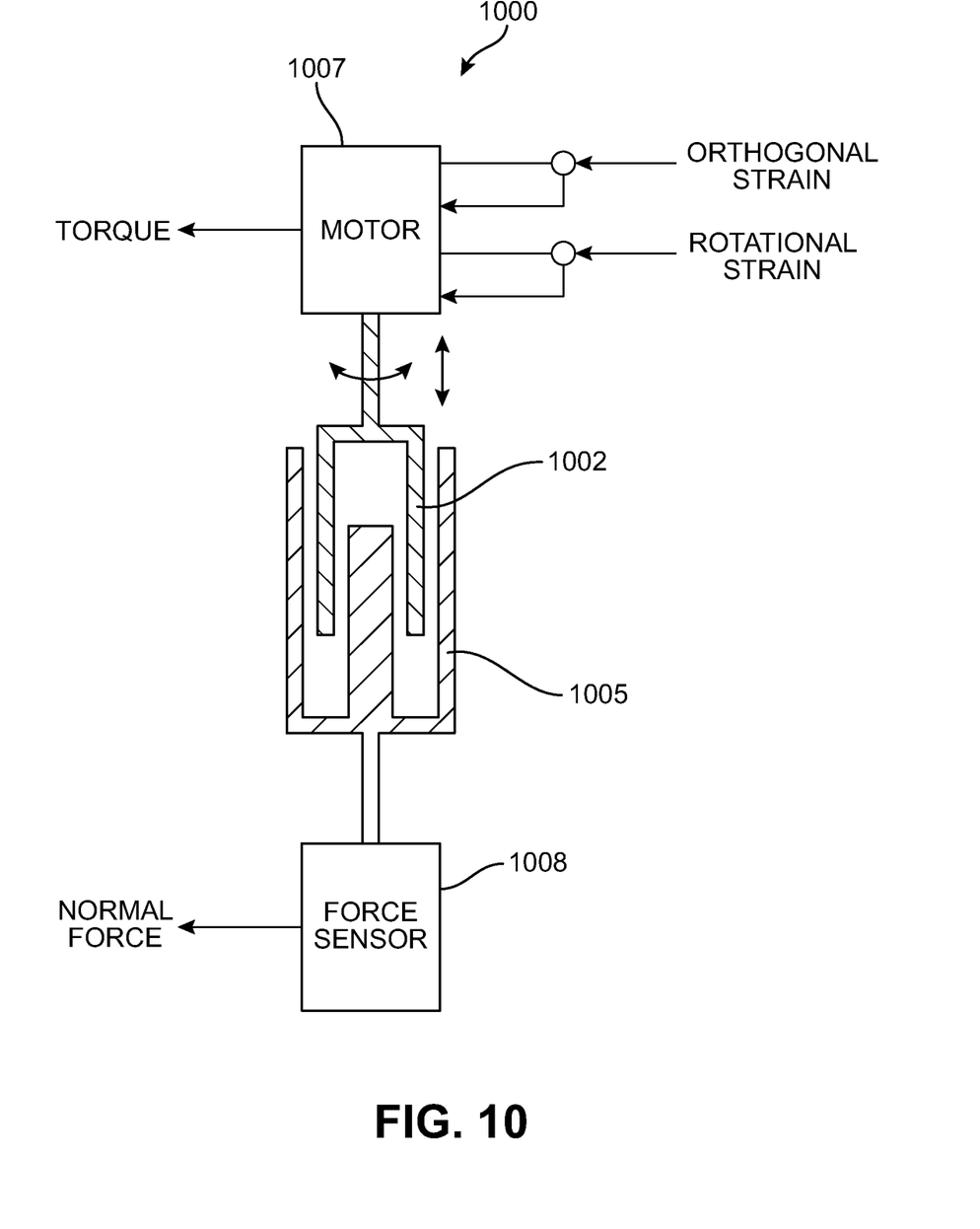
FIG. 10 is a schematic drawing of an OSP test module mounted on a single head rheometer with a separate force sensor.

Embodiments of the test modules disclosed herein may be used with a variety of rheometer configurations. For example, FIGS. 8, 9 and 10 are schematic diagrams of several alternative configurations for the test module in the rheometer. Other configurations may also be implemented by those of skill in the art.

In the embodiment shown in FIG. 8, transducer 803 in rheometer 800 is coupled to cylindrical bob 802. Cylindrical bob 802 imparts axial (i.e., vertical) deformation onto the test material in double wall cup 805. Motor 806 rotates double wall cup 805. Transducer 803 measures the torque applied to cylindrical bob 802 as the test material rotates in double wall cup 805. Transducer 803 also measures the normal force applied to cylindrical bob 802 in order to achieve the predetermined axial movement of cylindrical bob 802.

In the embodiment shown schematically in FIG. 9, motor 907 (consisting of a rotational actuator and a linear actuator) in rheometer 900 applies both the rotational strain and an axial (i.e., vertical) strain to the test material in double wall cup 905, via cylindrical bob 902. It also reports the normal force necessary to impose the orthogonal strain and the torque required to impose the rotational strain. In the embodiment shown in FIG. 10, motor 1007 applies both the rotational strain and the orthogonal axial strain to the test material in double wall cup 1005. Motor 1007 also measures the torque required to rotate cylindrical bob 1002. Force sensor 1008 measures the normal force experienced by double wall cup 1005 in response to the axial strain applied to the test material.

Embodiments of the test modules disclosed herein have achieved improvements in accuracy of 10% (for higher viscosity materials) up to 50% (for lower viscosity materials), compared to prior art test modules.

The test modules described herein and shown schematically in the figures may be used, for example, with a TA Instruments model ARES-G2 rheometer, available from TA Instruments, New Castle, Del., or with any other rheometer that is compatible with the embodiments of the test module described herein.

While various embodiments have been described above, the description is intended to be exemplary, rather than limiting. It will be apparent to those of ordinary skill in the art that additional embodiments and implementations are possible. Accordingly, the embodiments are not to be restricted except in light of the attached claims and their equivalents.

What is claimed is:

1. A rotational rheometer comprising:
    a double wall cup having an inner cylindrical wall and an outer cylindrical wall forming an annular chamber and a central cylindrical chamber;
    a cylindrical bob having a top disk portion attached to a hollow cylindrical portion by a plurality of legs, the plurality of legs having straight edges from the top disk portion to the hollow cylindrical portion, wherein the hollow cylindrical portion is dimensioned to fit within the annular chamber of the double wall cup;
    a motor coupled to the double wall cup configured to rotate the double wall cup;
    a transducer coupled to the cylindrical bob via a shaft attached to a center of the top disk portion configured to impose axial oscillations on the cylindrical bob;
    wherein the inner cylindrical wall of the double wall cup comprises openings at a lower end of the inner cylindrical wall that allow fluid communication from the annular chamber to the central cylindrical chamber;
    wherein the cylindrical bob has apertures below the top disk portion that circumscribe a substantial portion of a circumference of the top disk portion and a substantial portion of the circumference of the hollow cylindrical portion;
    wherein the annular chamber is configured to contain a fluid to be tested during operation of the rotational rheometer;

wherein, during operation of the rotational rheometer, the fluid has a top surface that is in contact with the plurality of legs above the hollow cylindrical portion of the cylindrical bob and below the top disk portion of the cylindrical bob; and wherein the apertures arranged between the plurality of legs reduce a total surface area of a meniscus of the fluid that is contact with the cylindrical bob, as the rotational rheometer operates, such that the top surface of the fluid is flat across the apertures, resulting in a reduction of a total surface tension effect attributed to the meniscus formed against the cylindrical bob wherein the legs are configured to reduce surface tension due to menisci formed between the hollow cylindrical portion of the cylindrical bob and the top disk portion of the cylindrical bob by the top surface of the fluid against the legs.

2. The rotational rheometer of claim 1, wherein the apertures circumscribe at least 80% of the circumference of the hollow cylindrical portion of the cylindrical bob, such that the plurality of legs occupy a remaining percentage of the circumference.

3. The rotational rheometer of claim 2, wherein the apertures circumscribe at least 90% of the circumference of the hollow cylindrical portion of the cylindrical bob, such that the plurality of legs occupy a remaining percentage of the circumference.

4. The rotational rheometer of claim 1, further comprising a cylindrical plug in the central cylindrical chamber.

5. The rotational rheometer of claim 1, wherein the transducer imposes sinusoidal oscillations on the cylindrical bob.

6. The rotational rheometer of claim 1, wherein the oscillations have a frequency below about 100 Hz.

7. The rotational rheometer of claim 6, wherein the frequency of the oscillations is between 0.1 Hz and 10 Hz, inclusive.

8. The rotational rheometer of claim 1, wherein the amplitude of the oscillations is between 0 µms and 500 µms, inclusive.

9. A rotational rheometer comprising:
a double wall cup having an inner cylindrical wall and an outer cylindrical wall forming an annular chamber configured to contain a fluid to be tested during operation of the rotational rheometer and a central cylindrical chamber;
a cylindrical bob having a top disk portion, a hollow cylindrical portion configured to fit within the annular chamber, a shaft attached to a center of the top disk portion, and at least two legs at a top circumference of the hollow cylindrical portion attaching the hollow cylindrical portion to the top disk portion, the at least two legs having straight edges from the top disk portion to the hollow cylindrical portion;
means for rotating the double wall cup;
means for imposing axial oscillations on the cylindrical bob;
means for measuring a torque required to rotate the double wall cup; and
means for measuring a normal force required to impose the axial oscillations on the cylindrical bob;
wherein the cylindrical bob has apertures between the at least two legs below the top disk portion that circumscribe a substantial portion of a circumference of the top disk; and
wherein, during operation of the rotational rheometer, the fluid to be tested has a top surface which is positioned above the hollow cylindrical portion of the cylindrical bob and below the top disk portion of the cylindrical bob;
wherein the apertures arranged between the at least two legs reduce a total surface area of a meniscus of the fluid that is contact with the cylindrical bob, as the rotational rheometer operates, such that the top surface of the fluid is flat across the apertures, resulting in a reduction of a total surface tension effect attributed to the meniscus formed against the cylindrical bob.

10. The rotational rheometer of claim 9, wherein the inner cylindrical wall of the double wall cup comprises openings at a lower end that allow fluid communication from the annular chamber to the central cylindrical chamber.

11. A rotational rheometer comprising:
a double wall cup having an inner cylindrical wall and an outer cylindrical wall forming an annular chamber and a central cylindrical chamber; and a cylindrical bob having a top disk portion, a hollow cylindrical portion and a shaft attached to a center of the top disk portion;
a transducer coupled to the cylindrical bob configured to impose axial oscillations on the cylindrical bob;
wherein the inner cylindrical wall of the double wall cup comprises openings at a lower end that allow fluid communication from the annular chamber to the central cylindrical chamber;
wherein the top disk portion of the cylindrical bob is connected to the hollow cylindrical portion of the cylindrical bob by at least two legs leaving apertures just below the top disk portion that circumscribe a substantial portion of the circumference of the hollow cylindrical portion, the at least two legs having straight edges from the top disk portion to the hollow cylindrical portion;
wherein the hollow cylindrical portion of the cylindrical bob is positioned within the annular chamber, and the annular chamber contains a fluid to be tested during operation of the rotational rheometer;
wherein, during operation of the rotational rheometer, the fluid in the annular chamber has a top surface that is in contact with the at least two legs between the hollow cylindrical portion of the cylindrical bob and the top disk portion of the cylindrical bob; and
wherein the apertures arranged between the at least two legs reduce a total surface area of a meniscus of the fluid that is contact with the cylindrical bob, as the rotational rheometer operates, such that the top surface of the fluid is flat across the apertures, resulting in a reduction of a total surface tension effect attributed to the meniscus formed against the cylindrical bob.

12. The rotational rheometer of claim 11, wherein the cylindrical bob is fabricated from titanium and the double wall cup is fabricated from anodized aluminum.

13. The rotational rheometer of claim 11, further comprising a platinum resistance thermometer centrally positioned in a base of the double wall cup.

14. The rotational rheometer of claim 11, wherein the apertures circumscribe at least 80% of the circumference of the hollow cylindrical portion.

15. The rotational rheometer of claim 11, wherein the outer wall of the double wall cup is removable.

16. The rotational rheometer of claim 11, further comprising a base supporting the inner wall and the outer wall of the double wall cup.

17. The rotational rheometer of claim 11, wherein the legs have sides that slant inwardly to facilitate the flow of fluid across the legs.

18. The rotational rheometer of claim 11, wherein the top disk portion of the cylindrical bob is connected to the hollow cylindrical portion of the cylindrical bob by three legs.

19. A test module for a rotational rheometer comprising:
a double wall cup having an inner cylindrical wall, an outer cylindrical wall forming an annular chamber and a central cylindrical chamber, and a base; and
a cylindrical bob having a top disk portion, a hollow cylindrical portion and a shaft attached to a center of the top disk portion;
a shaft mounted on the top disk portion of the cylindrical bob configured to be coupled to a transducer configured to impose axial oscillations on the cylindrical bob;
wherein the top disk portion of the cylindrical bob is connected to the hollow cylindrical portion of the cylindrical bob by at least two legs leaving apertures just below the top disk portion that circumscribe at least 80% of the circumference of the hollow cylindrical portion, the at least two legs having straight edges from the top disk portion to the hollow cylindrical portion;
wherein the hollow cylindrical portion is configured to be inserted within the annular chamber;
wherein the annular chamber is configured to contain a fluid to be tested during operation of the rotational rheometer such that, during operation of the rheometer, the fluid has a top surface that is positioned above the hollow cylindrical portion of the cylindrical bob and below the top disk portion of the cylindrical bob;
wherein the apertures arranged between the at least two legs reduce a total surface area of a meniscus of the fluid that is contact with the cylindrical bob, as the rotational rheometer operates, such that the top surface of the fluid is flat across the apertures, resulting in a reduction of a total surface tension effect attributed to the meniscus formed against the cylindrical bob.

20. The test module of claim 19, wherein the inner cylindrical wall of the double wall cup comprises openings at a lower end that allow fluid communication from the annular chamber to the central cylindrical chamber.

21. The test module of claim 19, wherein sides of the at least two legs slant inwardly to facilitate the flow of fluid across the at least two legs.

22. The test module of claim 19, wherein the top disk portion of the cylindrical bob is connected to the hollow cylindrical portion of the cylindrical bob by three legs, and wherein the three legs have sides that slant inwardly.

23. The test module of claim 19, wherein the cylindrical bob is fabricated from titanium and the double wall cup is fabricated from anodized aluminum.

24. The test module of claim 19, wherein the double wall cup is fabricated from a material that has a high thermal conductivity.

25. The test module of claim 19, wherein the outer cylindrical wall is attached to the base of the double wall cup using a bayonet mount.

26. A rotational rheometer comprising:
a double wall cup having an inner cylindrical wall and an outer cylindrical wall forming an annular chamber and a central cylindrical chamber;
a cylindrical bob having a top disk portion attached to a hollow cylindrical portion by a plurality of legs, wherein the hollow cylindrical portion is dimensioned to fit within the annular chamber of the double wall cup;
a motor coupled to the double wall cup configured to rotate the double wall cup;
a transducer coupled to the cylindrical bob via a shaft attached to a center of the top disk portion configured to impose axial oscillations on the cylindrical bob;
wherein the inner cylindrical wall of the double wall cup comprises openings at a lower end of the inner cylindrical wall that allow fluid communication from the annular chamber to the central cylindrical chamber;
wherein the cylindrical bob has apertures below the top disk portion that circumscribe a substantial portion of a circumference of the top disk portion and a substantial portion of the circumference of the hollow cylindrical portion;
wherein the annular chamber is configured to contain a fluid to be tested during operation of the rotational rheometer;
wherein, during operation of the rotational rheometer, the fluid has a top surface that is in contact with the plurality of legs above the hollow cylindrical portion of the cylindrical bob and below the top disk portion of the cylindrical bob; and
wherein the apertures arranged between the plurality of legs reduce a total surface area of a meniscus of the fluid that is contact with the cylindrical bob, as the rotational rheometer operates, such that the top surface of the fluid is flat across the apertures, resulting in a reduction of a total surface tension effect attributed to the meniscus formed against the cylindrical bob.

* * * * *